(12) United States Patent
McGonigle et al.

(10) Patent No.: US 8,444,570 B2
(45) Date of Patent: May 21, 2013

(54) SIGNAL PROCESSING TECHNIQUES FOR AIDING THE INTERPRETATION OF RESPIRATION SIGNALS

(75) Inventors: Scott McGonigle, Edinburgh (GB); Paul S. Addison, Edinburgh (GB); James N. Watson, Dunfermline (GB)

(73) Assignee: Nellcor Puritan Bennett Ireland, Mervue, Galway (IE)

( * ) Notice: Subject to any disclaimer, the term of this patent is extended or adjusted under 35 U.S.C. 154(b) by 815 days.

(21) Appl. No.: 12/481,045

(22) Filed: Jun. 9, 2009

(65) Prior Publication Data

US 2010/0312075 A1    Dec. 9, 2010

(51) Int. Cl.
*A61B 5/08*    (2006.01)

(52) U.S. Cl.
USPC ............................. 600/529; 600/538

(58) Field of Classification Search
USPC .................................. 600/529, 538
See application file for complete search history.

(56) References Cited

U.S. PATENT DOCUMENTS

| | | | |
|---|---|---|---|
| 3,532,087 A | 10/1970 | Horn | |
| 3,678,296 A * | 7/1972 | Day | 327/15 |
| 3,884,219 A | 5/1975 | Richardson et al. | |
| 3,926,177 A | 12/1975 | Hardway et al. | |
| 3,976,052 A * | 8/1976 | Junginger et al. | 600/484 |
| 4,289,141 A | 9/1981 | Cormier | |
| 4,696,307 A | 9/1987 | Montgieux | |
| 5,143,078 A | 9/1992 | Mather | |
| 5,273,036 A | 12/1993 | Kronberg | |
| 5,439,483 A | 8/1995 | Duong-Van | |
| 5,575,284 A | 11/1996 | Athan et al. | |
| 5,590,650 A | 1/1997 | Genova | |
| 5,632,272 A | 5/1997 | Diab et al. | |
| 5,680,871 A | 10/1997 | Ganshorn | |
| 5,682,898 A | 11/1997 | Aung | |
| 5,778,881 A | 7/1998 | Sun et al. | |
| 5,795,304 A | 8/1998 | Sun et al. | |
| 5,797,840 A | 8/1998 | Akselrod | |
| 5,827,195 A | 10/1998 | Lander | |
| 5,967,995 A | 10/1999 | Shusterman et al. | |
| 6,002,952 A | 12/1999 | Diab et al. | |

(Continued)

FOREIGN PATENT DOCUMENTS

| | | |
|---|---|---|
| JP | 09-084776 | 3/1997 |
| WO | WO 00/21438 | 4/2000 |

(Continued)

OTHER PUBLICATIONS

PCT International Search Report, Agent File RE PE953783WO, Intl Application No. PCT/GB2010/000837, Intl Filing Date: Apr. 26, 2010, Priority Date: Sep. 6, 2009, Applicant: Nellcor Puritan Bennett Ireland.

(Continued)

*Primary Examiner* — Navin Natnithithadha
*Assistant Examiner* — Michael R Bloch

(57) ABSTRACT

According to embodiments, a respiration signal may be processed to normalize respiratory feature values in order to improve and/or simplify the interpretation and subsequent analysis of the signal. Data indicative of a signal may be received at a sensor and may be used to generate a respiration signal. Signal peaks in the respiration signal may be identified and signal peak thresholds may be determined. The identified signal peaks may be adjusted based on the signal peak threshold values to normalize the respiration signal.

22 Claims, 13 Drawing Sheets

U.S. PATENT DOCUMENTS

| | | | |
|---|---|---|---|
| 6,036,653 A | 3/2000 | Baba et al. |
| 6,094,592 A | 7/2000 | Yorkey |
| 6,095,984 A | 8/2000 | Amano et al. |
| 6,117,075 A | 9/2000 | Barnea |
| 6,129,675 A | 10/2000 | Jay |
| 6,135,966 A | 10/2000 | Ko |
| 6,142,953 A | 11/2000 | Burton |
| 6,171,257 B1 | 1/2001 | Weil et al. |
| 6,171,258 B1 | 1/2001 | Karakasoglu et al. |
| 6,208,951 B1 | 3/2001 | Kumar et al. |
| 6,293,915 B1 | 9/2001 | Amano et al. |
| 6,306,088 B1 * | 10/2001 | Krausman et al. ............ 600/301 |
| 6,325,761 B1 | 12/2001 | Jay |
| 6,361,501 B1 | 3/2002 | Amano et al. |
| 6,393,311 B1 | 5/2002 | Edgar, Jr. et al. |
| 6,398,727 B1 | 6/2002 | Bui et al. |
| 6,561,986 B2 | 5/2003 | Baura |
| 6,608,934 B2 | 8/2003 | Scheirer |
| 6,654,623 B1 | 11/2003 | Kastle |
| 6,702,752 B2 | 3/2004 | Dekker |
| 6,709,402 B2 | 3/2004 | Dekker |
| 6,801,798 B2 | 10/2004 | Geddes et al. |
| 6,810,277 B2 | 10/2004 | Edgar, Jr. et al. |
| 6,811,538 B2 | 11/2004 | Westbrook et al. |
| 6,896,661 B2 | 5/2005 | Dekker |
| 6,918,878 B2 | 7/2005 | Brodnick |
| 6,930,608 B2 | 8/2005 | Grajales et al. |
| 6,931,269 B2 | 8/2005 | Terry |
| 6,990,426 B2 | 1/2006 | Yoon et al. |
| 7,001,337 B2 | 2/2006 | Dekker |
| 7,020,507 B2 | 3/2006 | Scharf |
| 7,035,679 B2 | 4/2006 | Addison |
| 7,043,293 B1 | 5/2006 | Baura |
| 7,052,469 B2 | 5/2006 | Minamiura et al. |
| 7,054,453 B2 | 5/2006 | Causevic |
| 7,054,454 B2 | 5/2006 | Causevic et al. |
| 7,079,888 B2 | 7/2006 | Oung |
| 7,171,251 B2 | 1/2007 | Sarussi |
| 7,171,269 B1 | 1/2007 | Addison |
| 7,173,525 B2 | 2/2007 | Albert |
| 7,203,267 B2 | 4/2007 | De Man et al. |
| 7,225,013 B2 | 5/2007 | Geva et al. |
| 7,246,618 B2 | 7/2007 | Habashi |
| 7,254,500 B2 | 8/2007 | Makeig |
| 7,289,835 B2 | 10/2007 | Mansfield |
| 7,344,497 B2 | 3/2008 | Kline |
| 7,381,185 B2 | 6/2008 | Zhirnov et al. |
| 7,398,115 B2 | 7/2008 | Lynn |
| 7,421,296 B1 | 9/2008 | Benser |
| 7,515,949 B2 | 4/2009 | Norris |
| 7,519,488 B2 | 4/2009 | Fu |
| 7,523,011 B2 | 4/2009 | Akiyama et al. |
| 2003/0028221 A1 * | 2/2003 | Zhu et al. ..................... 607/9 |
| 2003/0163057 A1 | 8/2003 | Flick et al. |
| 2003/0212336 A1 | 11/2003 | Lee et al. |
| 2005/0022606 A1 | 2/2005 | Partin et al. |
| 2005/0043616 A1 | 2/2005 | Chinchoy |
| 2005/0070774 A1 | 3/2005 | Addison et al. |
| 2005/0109340 A1 | 5/2005 | Tehrani |
| 2005/0215915 A1 | 9/2005 | Noda et al. |
| 2005/0222502 A1 | 10/2005 | Cooper |
| 2005/0251056 A1 | 11/2005 | Gribkov et al. |
| 2006/0074333 A1 | 4/2006 | Huiku |
| 2006/0155206 A1 | 7/2006 | Lynn |
| 2006/0209631 A1 | 9/2006 | Melese et al. |
| 2006/0211930 A1 | 9/2006 | Scharf et al. |
| 2006/0217603 A1 | 9/2006 | Nagai et al. |
| 2006/0229519 A1 | 10/2006 | Fujiwara et al. |
| 2006/0241506 A1 | 10/2006 | Melker et al. |
| 2006/0258921 A1 | 11/2006 | Addison et al. |
| 2006/0265022 A1 | 11/2006 | John et al. |
| 2006/0282001 A1 | 12/2006 | Noel et al. |
| 2007/0021673 A1 | 1/2007 | Arbel et al. |
| 2007/0073120 A1 | 3/2007 | Li et al. |
| 2007/0073124 A1 | 3/2007 | Li et al. |
| 2007/0129647 A1 | 6/2007 | Lynn |
| 2007/0149883 A1 | 6/2007 | Yesha |
| 2007/0167694 A1 | 7/2007 | Causevic et al. |
| 2007/0167851 A1 | 7/2007 | Vitali et al. |
| 2007/0282212 A1 | 12/2007 | Sierra et al. |
| 2008/0045832 A1 | 2/2008 | McGrath |
| 2008/0060138 A1 | 3/2008 | Price et al. |
| 2008/0076992 A1 | 3/2008 | Hete et al. |
| 2008/0082018 A1 | 4/2008 | Sackner et al. |
| 2008/0171946 A1 | 7/2008 | Hansmann |
| 2008/0190430 A1 | 8/2008 | Melker et al. |
| 2008/0202525 A1 | 8/2008 | Mitton et al. |
| 2008/0214903 A1 | 9/2008 | Orbach |
| 2008/0243021 A1 | 10/2008 | Causevic et al. |

FOREIGN PATENT DOCUMENTS

| | | |
|---|---|---|
| WO | WO 01/25802 | 4/2001 |
| WO | WO 01/62152 | 8/2001 |
| WO | WO 01/76471 | 10/2001 |
| WO | WO 03/000125 | 1/2003 |
| WO | WO 03/055395 | 7/2003 |
| WO | WO 2004/075746 | 9/2004 |
| WO | WO 2004/105601 | 12/2004 |
| WO | WO 2005/096170 | 10/2005 |
| WO | WO 2006/085120 | 8/2006 |
| WO | WO 2008/043864 | 8/2008 |
| WO | 2010/001248 A2 | 1/2010 |

OTHER PUBLICATIONS

Addison, Paul S., The Illustrated Wavelet Transform Handbook, Taylor & Francis Group, 2002.

Addison, Paul, "The Little Wave with the Big Future," Physics World, Mar. 2004, pp. 35-39.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.

Leonard, Paul A., Douglas, J. Graham, Grubb, Neil R., Clifton, David, Addison, Paul S., Watson, James N., "A Fully Automated Algorithm for the Determination of Respiratory Rate From the Photoplethysmogram," Journal of Clinical Monitoring and Computing, 2006.

Leonard, Paul A., Clifton, David, Addison, Paul S., Watson, James N., Beattie, Tom "An Automated Algorithm for Determining Respiratory Rate by Photoplethysmogram in Children," Acta Paediatricia, 2006; 95: 1124-1128.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Yamada, Michio, "Wavelet Analysis and Its Application," Journal of the Institute of Electronics, Information and Communication Engineers, vol. 76, No. 5, May 1993, pp. 518-528.

\* cited by examiner

SIGNAL PROCESSING TECHNIQUES FOR AIDING THE INTERPRETATION OF RESPIRATION SIGNALS

SUMMARY

The present disclosure is related to signal processing systems and methods, and more particularly, to systems and methods for processing respiration signals.

In an embodiment, a respiration signal may be processed to normalize respiratory feature values of the signal. Respiration signals may indicate the breathing patterns of a patient over time. Respiratory features (e.g., signal peaks) within the respiration signal may reflect the breathing of the patient. Respiratory features within the respiration signal may also reflect noise or other artifacts. The respiration signal may be normalized by reducing variations in the respiratory feature values within the respiration signal. Normalizing the respiration signal may reduce the effect of noise or other artifacts on the respiration signal and may aid in the interpretation and/or analysis of the respiration signal. For example, normalizing the respiration signal may aid in the determination of respiration parameters such as respiration rate.

In an embodiment, a respiration signal may be obtained using a sensor capable of measuring the respiration of a patient or by deriving the respiration signal from another suitable biosignal. Respiratory features such as signal peaks (e.g., local maxima and/or minima in the signal amplitude versus time) in the respiration signal may be identified and signal peak thresholds may be determined. In an embodiment, signal peak threshold values may be determined based on the values of the identified signal peaks. For example, signal peak threshold values may be related to a mean value, a weighted mean value, a median value, a value at a certain percentile of distribution of values, or any other suitable value. An upper signal peak threshold value may be used to identify signal peaks having values that exceed a particular value. A lower signal peak threshold value may be used to identify signal peaks having values that are below a particular value. The identified signal peaks may then be adjusted based on the determined signal peak threshold values to normalize the respiration signal.

In an embodiment, a portion of the respiration signal surrounding an identified signal peak may be selected and the entire selected portion of the signal may be adjusted. For example, a signal segment may be a portion of the signal that begins at a zero crossing before an identified signal peak and ends at a zero crossing that after the signal peak. As another example, a signal segment may be the a portion of a signal that exceeds a threshold value.

In an embodiment, selected signal segments may be rescaled by a constant value. In an embodiment, selected signal segments may be nonlinearly rescaled based at least in part on a distance between a signal peak and another suitable value (e.g., a characteristic value of the signal or a threshold value).

For the purposes of illustration, and not by way of limitation, in an embodiment disclosed herein the respiration signal may be derived from a photoplethysmograph (PPG) signal drawn from any suitable source, such as a pulse oximeter. The PPG signal may be filtered, processed or otherwise transformed before the techniques described herein are applied to the signal. A scalogram may be generated from the PPG signal data. Respiratory features may be identified within the scalogram and/or within a secondary wavelet decomposition of the scalogram. A respiration signal may be generated from these identified respiratory features.

In an embodiment, a normalized respiration signal may be generated from a scalogram of wavelet phase information calculated from a PPG signal. A respiration ridge representing local phase values relating to respiratory features as a function of time may be identified within the scalogram. A sinusoidal function indicative of respiration phase and having normalized height values may then be generated from these local phase values.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Figure 1:
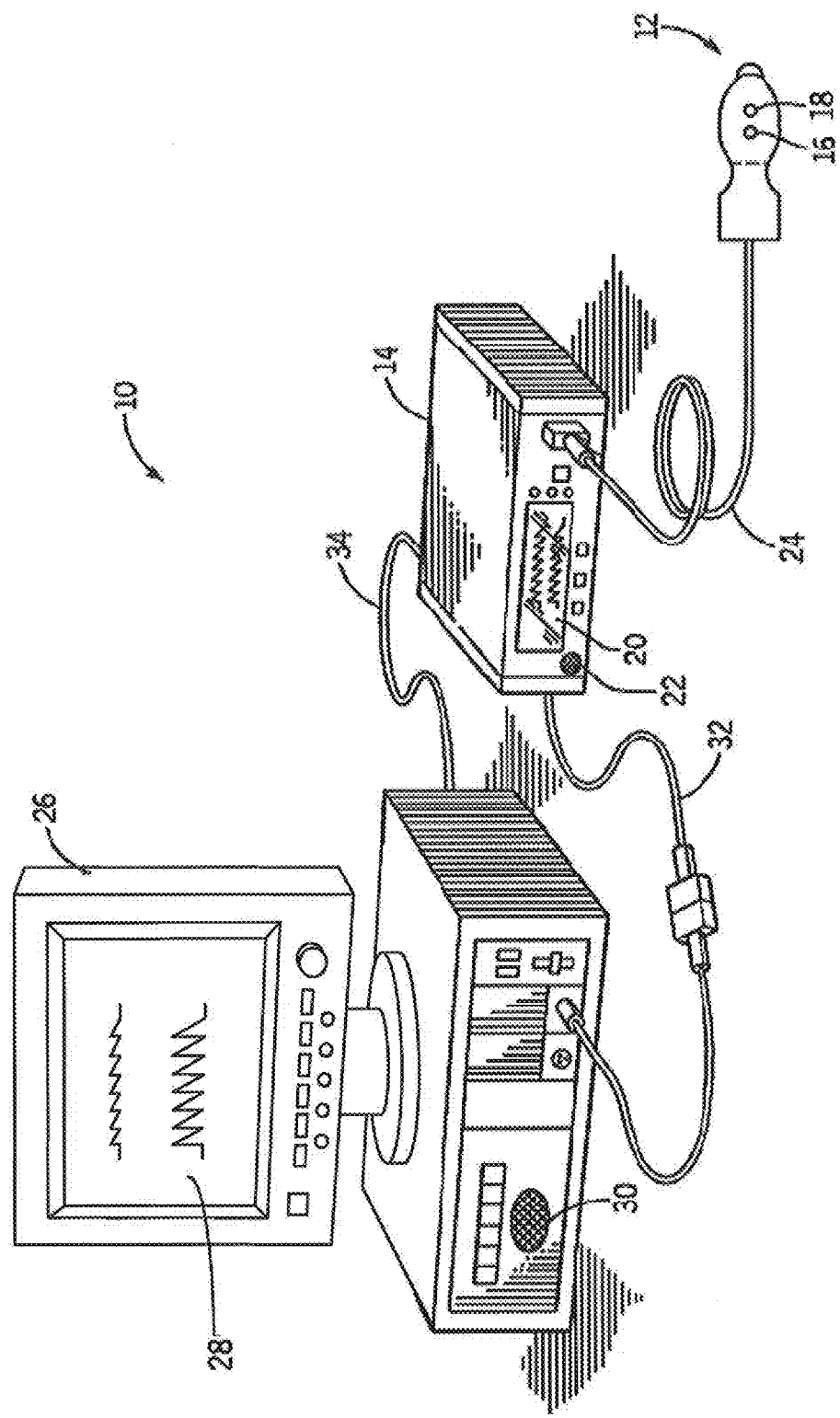
FIG. 1 shows an illustrative pulse oximetry system in accordance with an embodiment.

An oximeter is a medical device that may determine the oxygen saturation of the blood. One common type of oximeter is a pulse oximeter, which may indirectly measure the oxygen saturation of a patients blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t)=I_0(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_o$=intensity of light transmitted;
s=oxygen saturation;
$\beta_o$, $\beta_r$=empirically derived absorption coefficients; and
$l(t)$=a combination of concentration and path length from emitter to detector as a function of time.

The traditional approach measures light absorption at two wavelengths (e.g., red and infrared (IR)), and then calculates saturation by solving for the "ratio of ratios" as follows.
1. First, the natural logarithm of (1) is taken ("log" will be used to represent the natural logarithm) for IR and Red $$\log I=\log I_0-(s\beta_o+(1-s)\beta_r)l \quad (2)$$

2. (2) is then differentiated with respect to time $$\frac{d\log I}{dt}=-(s\beta_0+(1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_0(\lambda_R)+(1-s)\beta_r(\lambda_R)}{s\beta_0(\lambda_{IR})+(1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_0(\lambda_{IR})-\beta_r(\lambda_{IR})) - \frac{d\log I(\lambda_{IR})}{dt}(\beta_0(\lambda_R)-\beta_r(\lambda_R))}$$

Note in discrete time $$\frac{d\log I(\lambda,t)}{dt} \simeq \log I(\lambda,t_2)-\log I(\lambda,t_1)$$

Using log A-log B=log A/B, $$\frac{d\log I(\lambda,t)}{dt} \simeq \log\left(\frac{I(t_2,\lambda)}{I(t_1,\lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1,\lambda_R)}{I(t_2,\lambda_R)}\right)}{\log\left(\frac{I(t_1,\lambda_{IR})}{I(t_2,\lambda_{IR})}\right)} = R \quad (5)$$

where R represents the "ratio of ratios." Solving (4) for s using (5) gives $$s = \frac{\beta_r(\lambda_R)-R\beta_r(\lambda_{IR})}{R(\beta_0(\lambda_{IR})-\beta_r(\lambda_{IR}))-\beta_0(\lambda_R)+\beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{dI/dt}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2,\lambda_R)-I(t_1,\lambda_R)}{I(t_1,\lambda_R)}}{\frac{I(t_2,\lambda_{IR})-I(t_1,\lambda_{IR})}{I(t_1,\lambda_{IR})}} \quad (7)$$

$$= \frac{[I(t_2,\lambda_R)-I(t_1,\lambda_R)]I(t_1,\lambda_{IR})}{[I(t_2,\lambda_{IR})-I(t_1,\lambda_{IR})]I(t_1,\lambda_R)}$$

$$= R$$

which defines a cluster of points whose slope of y versus x will give R where $$x(t)=[I(t_2,\lambda_{IR})-I(t_1,\lambda_{IR})]I(t_1,\lambda_R)$$

$$y(t)=[I(t_2,\lambda_R)-I(t_1,\lambda_R)]I(t_1,\lambda_{IR})$$

$$y(t)=Rx(t) \quad (8)$$

FIG. 1 is a perspective view of an embodiment of a pulse oximetry system 10. System 10 may include a sensor 12 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's blood oxygen saturation generated by pulse oximetry monitor 14 (referred to as an "SpO$_2$" measurement), pulse rate information from monitor 14 and blood pressure from a blood pressure monitor (not shown) on display 28. Pulse oximetry system 10 may also include a speaker 30.

Monitor 14 may be communicatively coupled to multi-parameter patient monitor 26 via a cable 32 or 34 that is coupled to a sensor input port or a digital communications port, respectively and/or may communicate wirelessly (not shown). In addition) monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
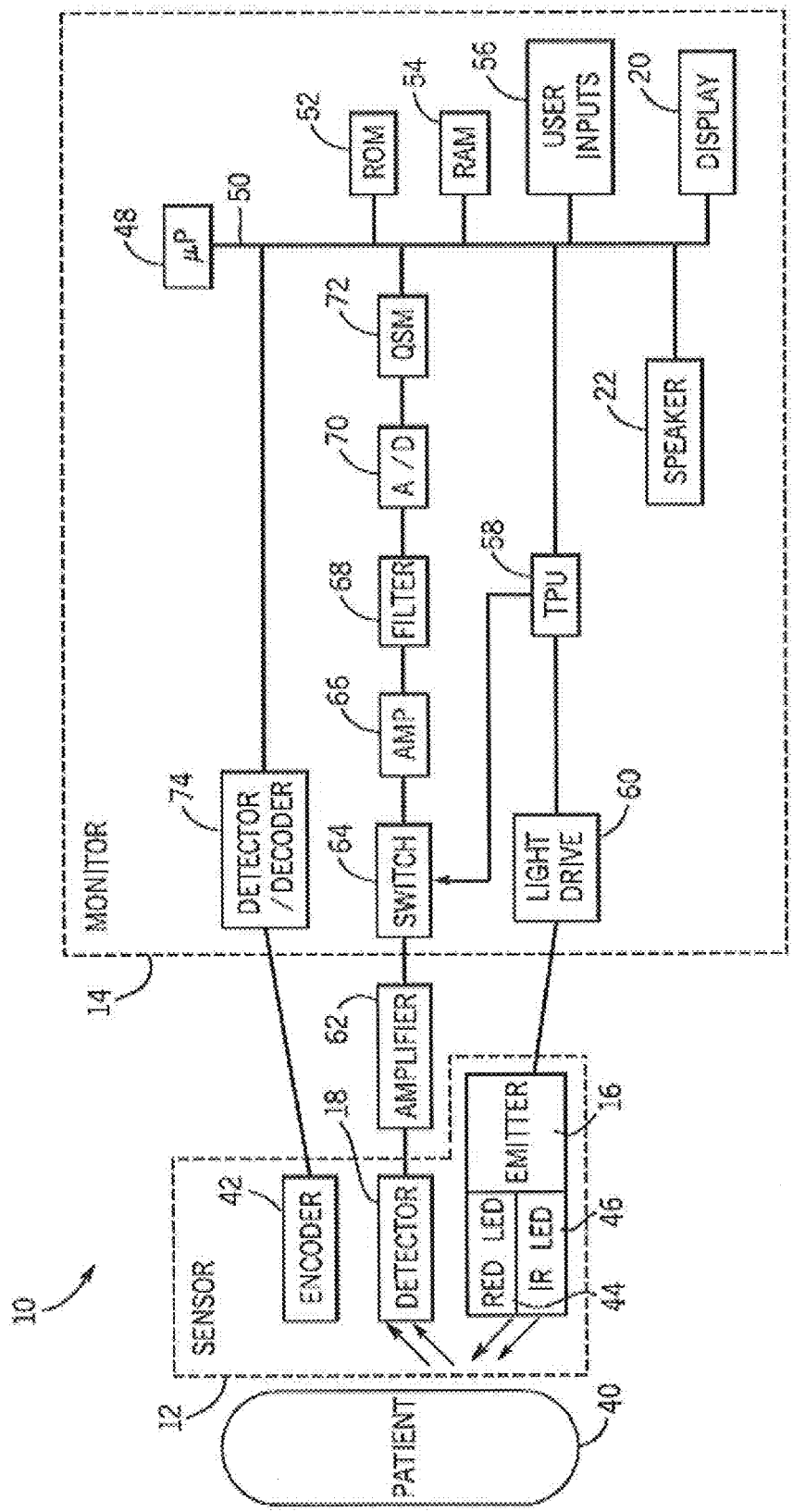
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patients tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/ID converter 70 for multiple light wavelengths or spectra received.

In an embodiment, microprocessor 48 may determine the patient's physiological parameters, such as $SpO_2$ and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physicians awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a, b) = \frac{1}{\sqrt{a}} \int_{-\infty}^{+\infty} x(t)\psi^*\left(\frac{t-b}{a}\right) dt \qquad (9)$$

where $\psi^*(t)$ is the complex conjugate of the wavelet function $\psi(t)$, a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to gainer more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b) = |T(a,b)|^2 \quad (10)$$

where '||' is the modulus operator. The scalogram may be rescaled for useful purposes. One common rescaling is defined as $$S_R(a, b) = \frac{|T(a, b)|^2}{a} \quad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unscaled wavelet representation, linear rescaling, any power of the modulus of the wavelet transform, or any other suitable rescaling. In addition, for purposes of clarity and conciseness, the term "scalogram" shall be taken to mean the wavelet transform, T(a, b) itself or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \quad (12)$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t) = \pi^{-1/4}(e^{i2\pi f_0 t} - e^{-(2\pi f_0)^2/2})e^{-t^2/2} \quad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \quad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figures 3A, 3B:
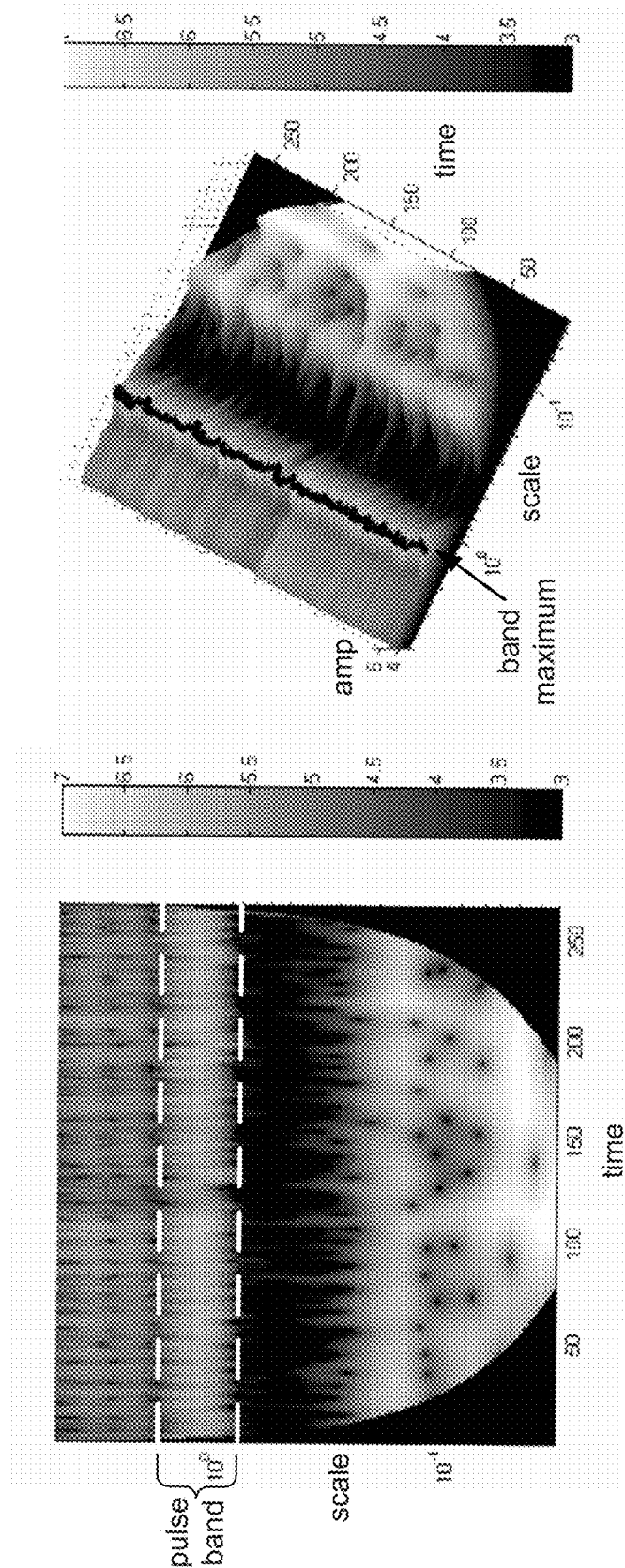
FIGS. 3(a) and 3(b) show illustrative views of a scalogram derived from a PPG signal in accordance with an embodiment.

Pertinent repeating features in a signal give rise to a time-scale band in wavelet space or a resealed wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable rescaling of the scalogram, such as that given in equation (11), the ridges found in wavelet space may be related to the instantaneous frequency of the signal. In this way, the pulse rate may be obtained from the PPO signal. Instead of resealing the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
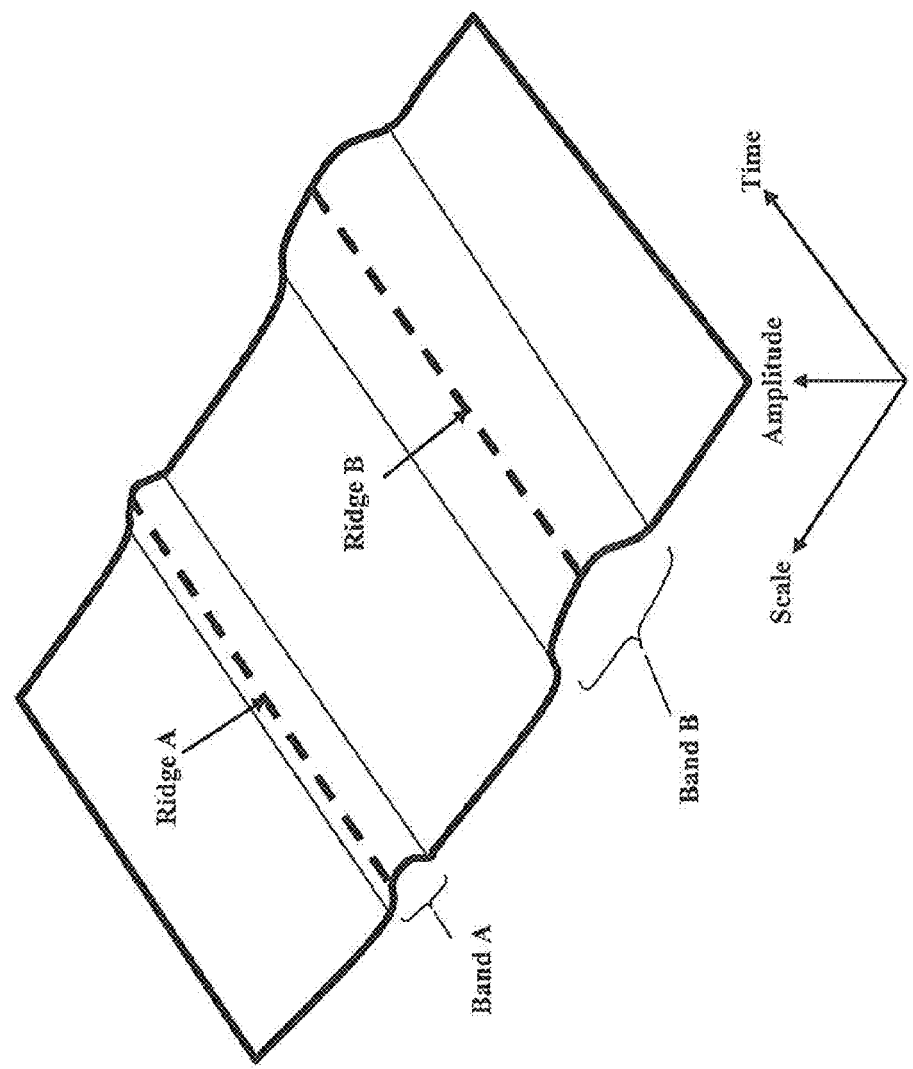
FIG. 3(c) shows an illustrative scalogram derived from a signal containing two pertinent components in accordance with an embodiment.
Figure 3D:
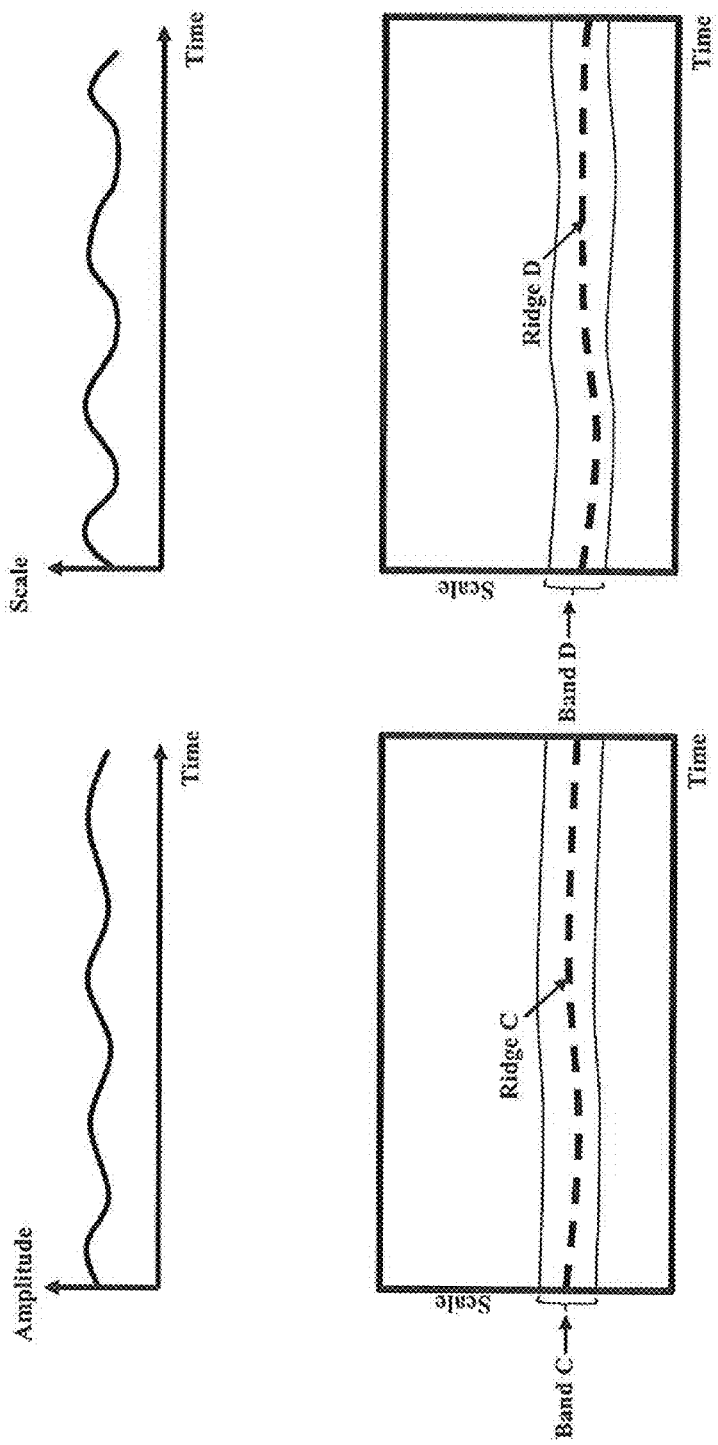
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a resealed wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a,b) \frac{1}{\sqrt{a}} \psi\left(\frac{t-b}{a}\right) \frac{da\,db}{a^2} \quad (15)$$

which may also be written as:

$$x(t) = \frac{1}{C_g} \int_{-\infty}^{\infty} \int_0^{\infty} T(a,b) \psi_{a,b}(t) \frac{da\,db}{a^2} \quad (16)$$

where $C_g$ is a scalar value known as the admissibility constant. It is wavelet type dependent and may be calculated from:

$$C_g = \int_0^{\infty} \frac{|\hat{\psi}(f)|^2}{f} df \quad (17)$$

Figure 3E:
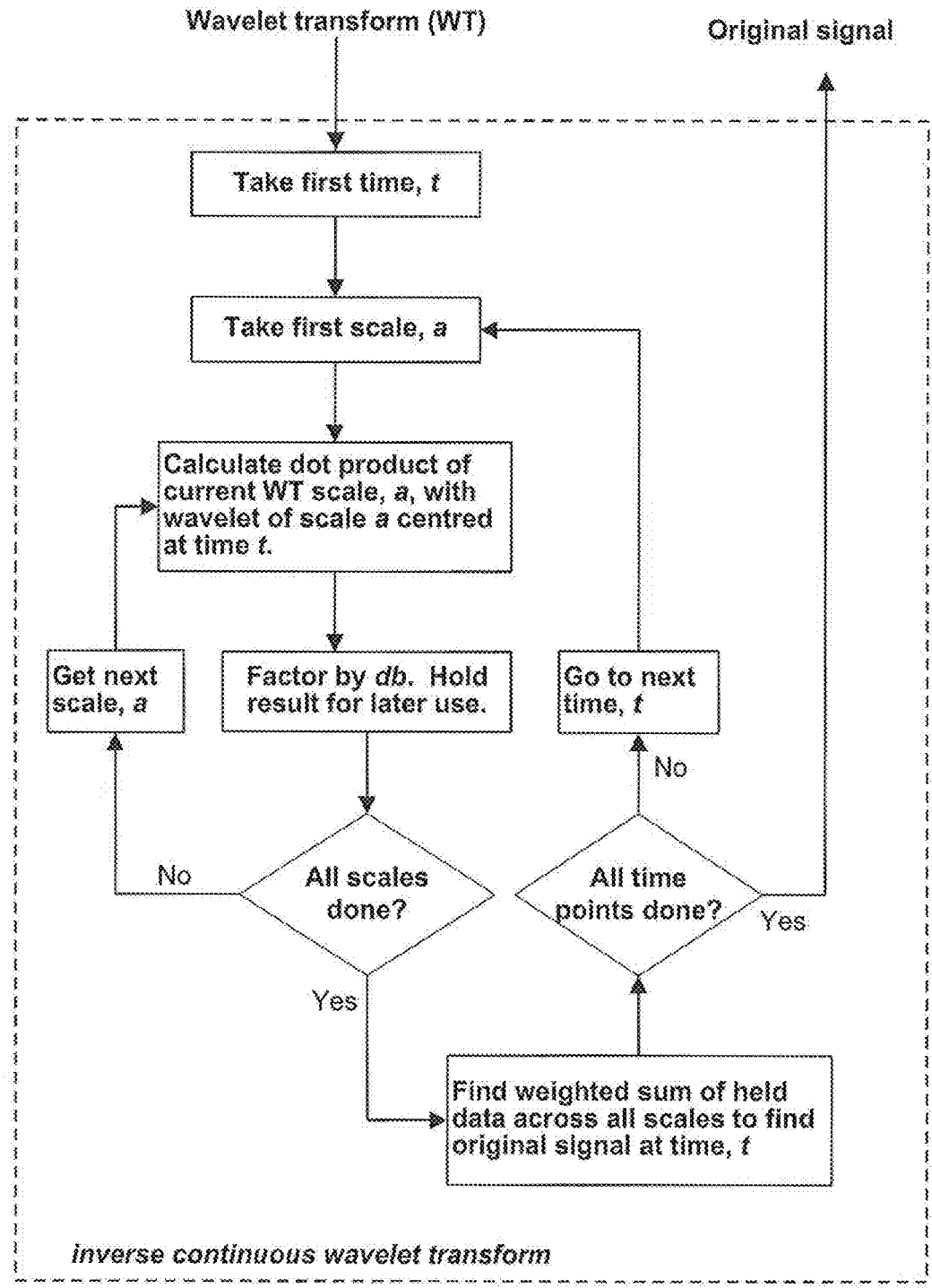
FIGS. 3(e) and 3(f) are flow charts of illustrative steps involved in performing an inverse continuous wavelet transform in accordance with embodiments.
Figure 3F:
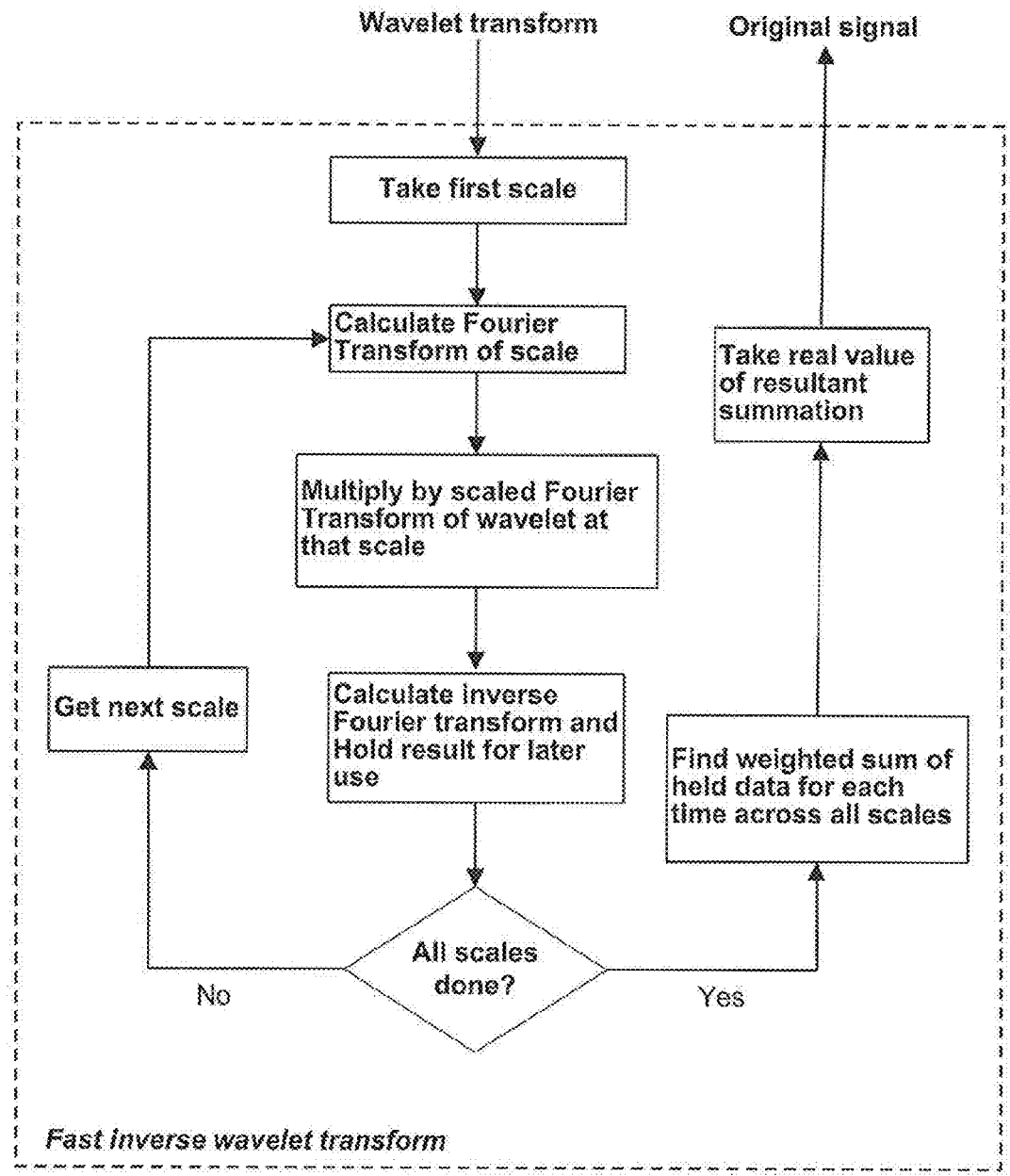

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

Figure 4:
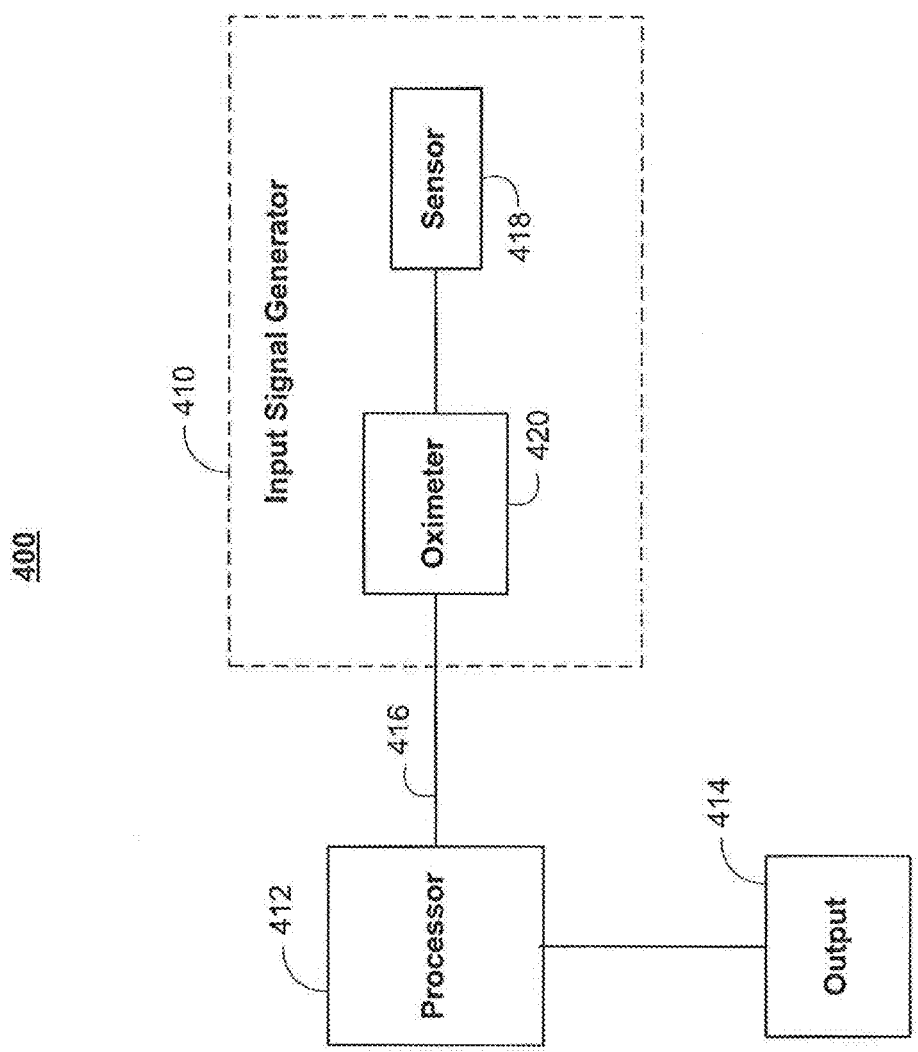
FIG. 4 is a block diagram of an illustrative continuous wavelet processing system in accordance with some embodiments.

FIG. 4 is an illustrative continuous wavelet processing system in accordance with an embodiment. In this embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14.

Figure 5:
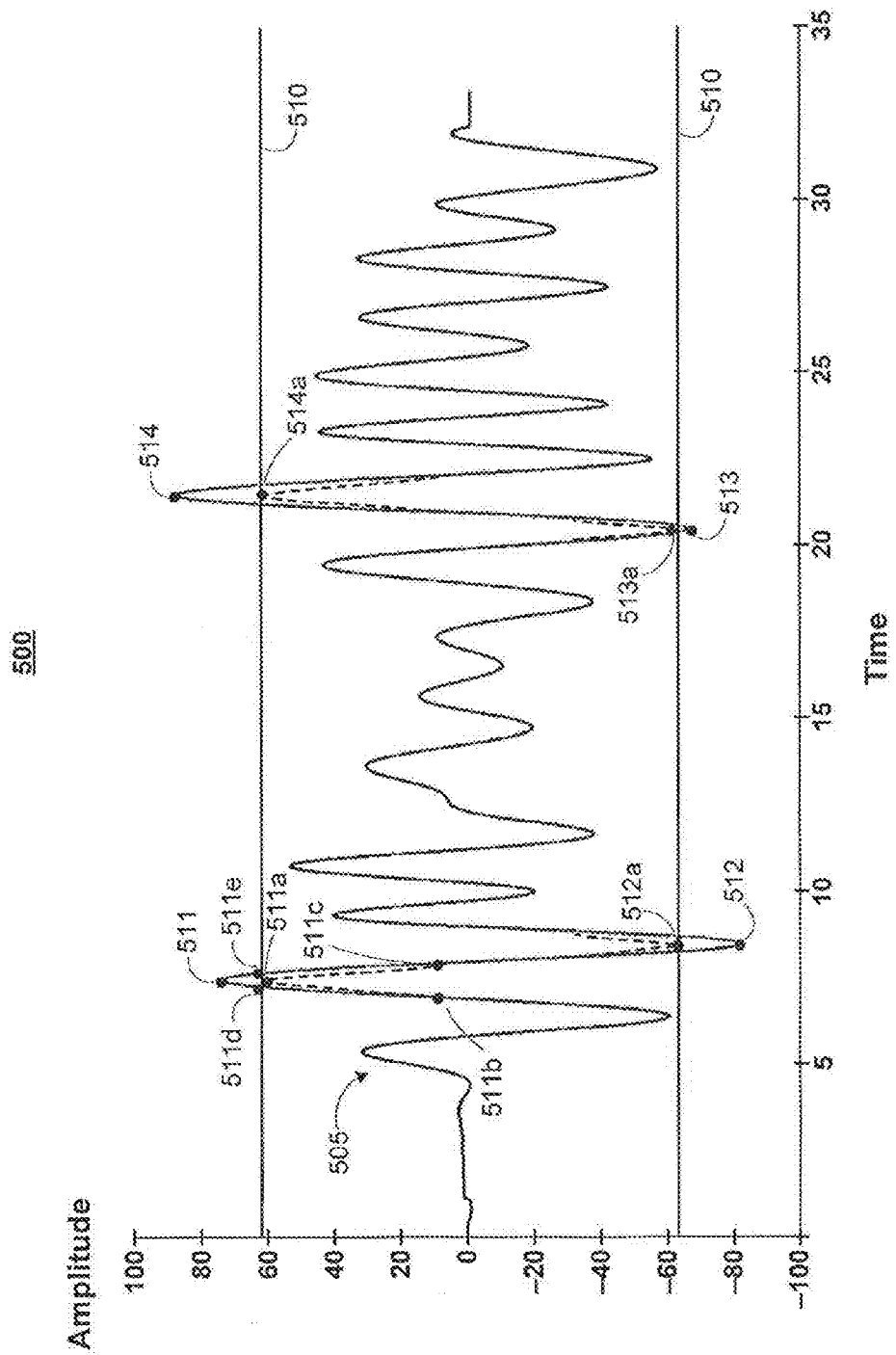
FIG. 5 is an illustrative plot of a respiration signal in accordance with an embodiment.

FIG. 5 is an illustrative plot 500 of a respiration signal 505. Respiration signal 505 may indicate the breathing patterns of a patient over time. Plot 500 displays time on the x-axis and signal amplitude values of respiration signal 505 on the y-axis. Plot 500 may be displayed using any suitable display device such as, for example, monitor 20 (FIG. 1), display 28 (FIG. 1), a PDA, a mobile device, or any other suitable display device. Additionally, plot 500 may be displayed on multiple display devices.

Respiration signal 505 may be obtained using a sensor capable of measuring the respiration of a patient, such as patient 40 (FIG. 2). For example, the respiration of a patient may be measured using a flow meter or a chest band sensor. Respiration signal 505 may also be derived from other biological signals (i.e., biosignals) captured by one or more sensors of a suitable biosignal measurement system. For example, respiration signal 505 may be derived from PPG signal data received from a pulse oximetry system such as pulse oximetry system 10 (FIG. 1). Respiration signal 505 may also be derived from other biosignals including transthoracic impedance signals, capnograph signals, nasal thermistor signals, and/or electrocardiogram (EKG) signals. The derivation of respiration signal 505 from a PPG signal or other suitable biosignal will be described in more detail below. Although, the techniques disclosed herein are described in terms of a respiration signal derived from a PPG signal, the disclosed techniques may be applied to any respiration signal or any other biosignals where cyclic phenomena are captured by the measurement system.

Respiration signal 505 may exhibit an oscillatory behavior versus time. The size, shape, and frequency of respiration signal 505 may be indicative of the breaths or breathing cycle of a patient, such as patient 40 (FIG. 2), and/or may be used determine the respiration rate of the patient. Respiration signal 505 may be a processed version of a preliminary respiration signal obtained from a sensor or derived from a suitable biosignal. The preliminary respiration signal may contain erroneous or otherwise undesirable artifacts due to, for example, patient movement, equipment failure, and/or various noise sources. For example, cable 24, cable 32, and/or cable 34 (all of FIG. 1) may malfunction or become loosened from the equipment to which it is connected. Further, sensor 12 (FIG. 1), or any constituent component of sensor 12 (FIG. 1) (for example, emitter 16 (FIG. 1) and/or detector 18 (FIG. 1)) may malfunction and/or become loosened. Additionally, noise sources may produce inconsistent features in a PPG signal or other biosignal from which respiration signal 505 was derived. Possible sources of noise include thermal noise, shot noise, flicker noise, burst noise, and/or electrical noise caused by light pollution. These and other noise sources may be introduced, for example, through sensor 12 (FIG. 1), and/or cables 24, 32, and 34 (all of FIG. 1). These and/or other phenomena may be present in a system such as pulse oximetry system 10 (FIG. 1), and thus may introduce inconsistent features into the measured PPG signal and in turn may introduce inconsistent features into respiration signal 505.

As shown in plot 500, respiration signal 505 may be substantially free of these erroneous and otherwise undesirable artifacts. The effect of these artifacts on a respiration signal may be reduced or eliminated by processing the underlying biosignal (e.g., a PPG signal) from which respiration signal 505 is derived, by the processing techniques used to derive respiration signal 505 from the biosignal and/or by processing a preliminary respiration signal to obtain respiration signal 505. Each of these processing steps may be implemented in a pulse oximetry system such as pulse oximetry system 10 (FIG. 1) and may be carried out using a processor such as processor 412 (FIG. 4) or microprocessor 48 (FIG. 2). However, even when these artifacts are reduced or eliminated, respiration signal 505 may still contain respiratory features (e.g., signal peaks) having a wide range of amplitude values. It may be advantageous to reduce the range of these amplitude values in respiration signal 505 in order to improve the interpretation and subsequent analysis of this signal and/or to obtain additional respiration parameters such as respiration rate. For example, one or more large signal peaks in respiration signal 505 may adversely effect the respiration rate determined from the signal.

Plot 500 of FIG. 5 includes upper threshold 510 to reduce the amplitude variations in respiration signal 505. Signal peaks having amplitude values that are above upper threshold 510 may be reduced. These signal peaks may be reduced to amplitude values that are closer to the threshold value, closer to a mean or median signal peak value for respiration signal 505 or closer to another predetermined value. For example, signal peaks 511, 512, 513, and 514 all have amplitude values that exceed upper threshold 510. These signal peaks may therefore be reduced to the values of adjusted signal peaks 511a, 512a, 513a, and 514a, which may be substantially equal to the value of upper threshold 510.

Figure 6:
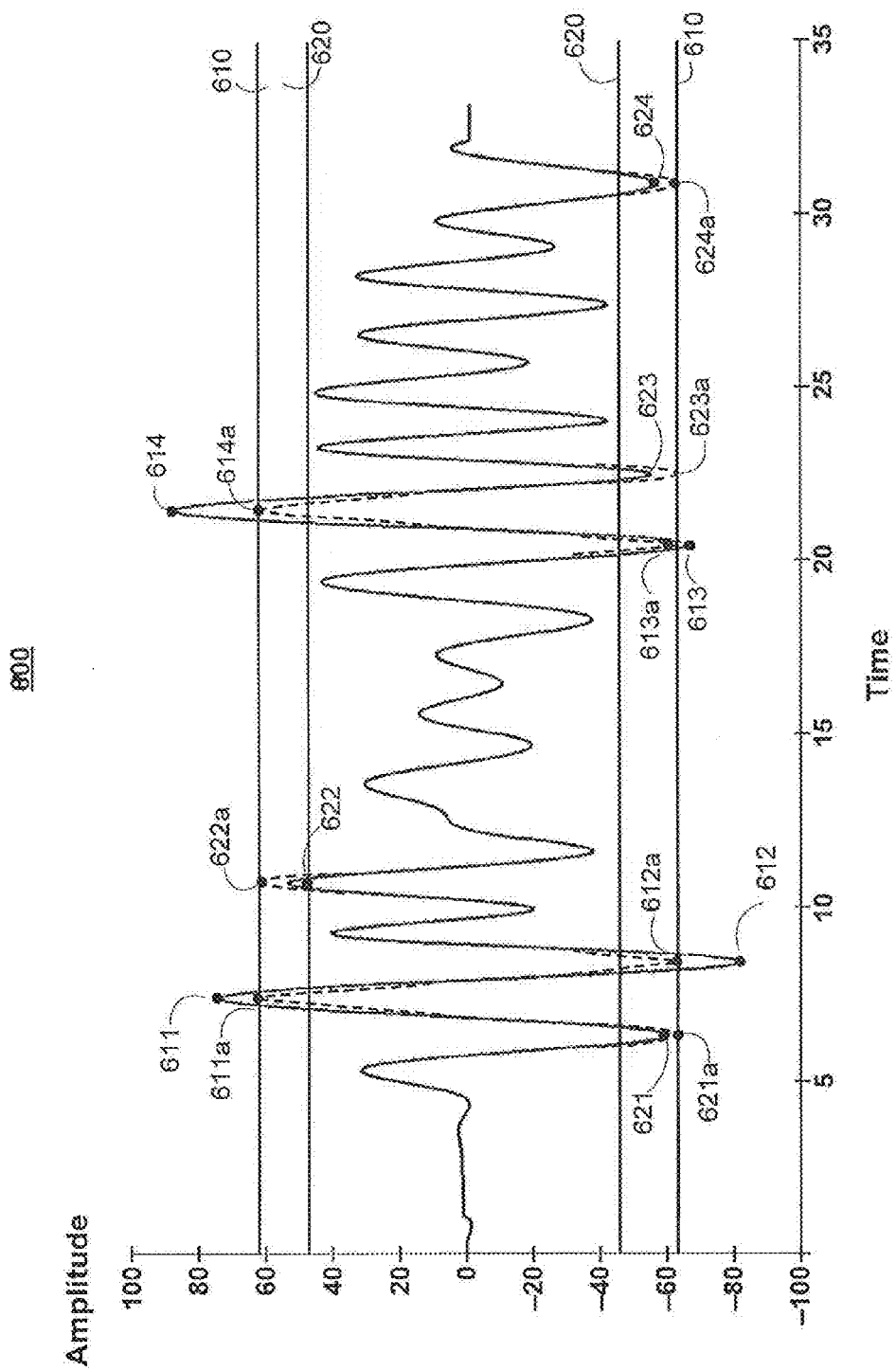
FIG. 6 is another illustrative plot of a respiration signal in accordance with an embodiment.

FIG. 6 is an illustrative plot 600 of a respiration signal 605 which is similar to plot 500 of FIG. 5 and includes additional, lower threshold 620. Signal peaks 611, 612, 613, and 614 all have amplitude values that exceed upper threshold 610 and may therefore be reduced to the values of adjusted signal peaks 611a, 612a, 613a, and 614a. Additionally or alternatively, signal peaks 621, 622, 623, and 624 all have amplitude values that are less than upper threshold 610 and that exceed lower threshold 620. The amplitude values of these signal peaks may be increased to the values of adjusted signal peaks 621a, 622a, 623a, and 624a. According to this example, amplitude values of signal peaks that exceed upper threshold 610 are reduced and signal peaks having values between lower threshold 620 and upper threshold 610 are be increased. In this manner, signal peaks having values both greater than and less than the value of upper threshold 610 may be adjusted closer to a single amplitude value, i.e., the value of upper threshold 610. Signal peaks having amplitude values that are less than lower threshold 620 may remain unchanged to prevent erroneously small features from being increased in amplitude. In another example, upper and lower signal threshold values may be set such that signal peak values that exceed an upper threshold value or that are less than a lower threshold value may be adjusted closer to a value between the two threshold values (e.g., a mean value). Signals peak values that are between these two threshold values may remain unchanged. Additionally, a third, minimum threshold value may prevent erroneously small features from being increased in amplitude.

Process 700 (depicted in FIG. 7) illustrates exemplary techniques for reducing amplitude variations in respiration signals 505 and 605 by normalizing the peak values of these signals based on one or more threshold values. Normalizing signal peaks within respiration signals 505 and 605 may reduce the amplitude variations of these respiration signal may improve and/or simplify the subsequent processing of these respiration signals. For example, normalizing signal peaks within respiration signals 505 and 605 may aid in the determination of respiration rate information from these signals.

Figure 7:
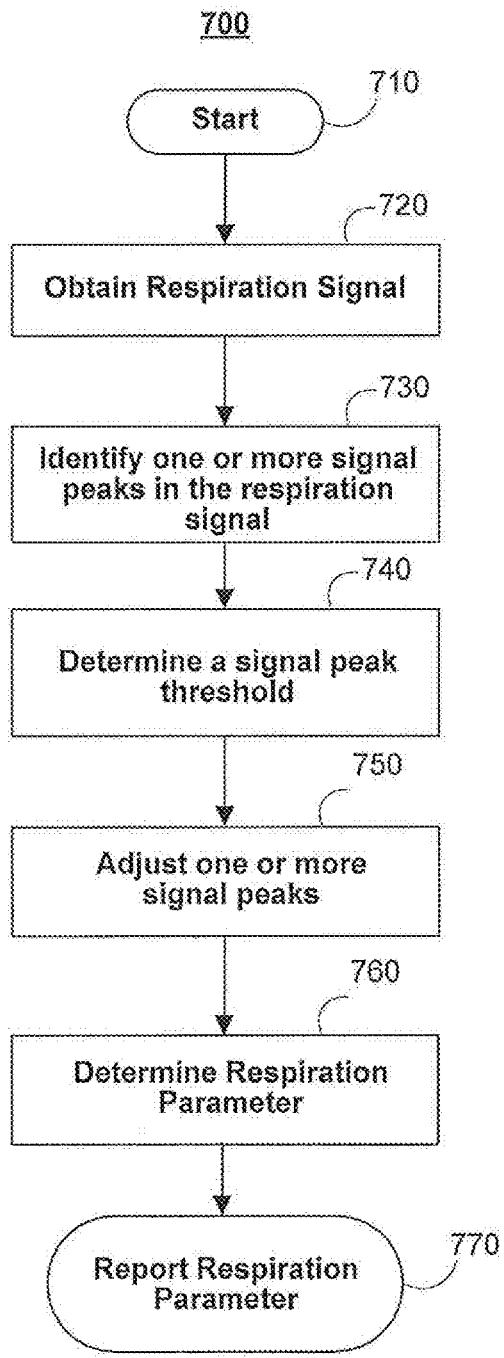
FIG. 7 depicts an illustrative process for normalizing respiratory feature values of a respiration signal in accordance with an embodiment.

FIG. 7 depicts an illustrative process 700 for normalizing respiratory feature amplitude values of a respiration signal (or parts of a respiration signal), e.g., respiration signal 505 (FIG. 5) or respiration signal 605 (FIG. 6). Process 700 may be implemented in a pulse oximetry system such as pulse oximetry system 10 (FIG. 1), and the steps of process 700 may be carried out using a processor such as processor 412 (FIG. 4) or microprocessor 48 (FIG. 2).

Process 700 may start at step 710. At step 720, process 700 may obtain a respiration signal. The respiration signal obtained in step 720 may be obtained using a sensor capable of measuring the respiration of a patient, such as patient 40 (FIG. 2). For example, the respiration of a patient may be measured using a flow meter or a chest band sensor. The respiration signal obtained in step 720 may also be derived from other biological signals (i.e., biosignals) captured by one or more sensors of a suitable biosignal measurement system. For example, respiration signal 505 may be derived from PPG signal data received from a pulse oximetry system such as pulse oximetry system 10 (FIG. 1) using a sensor such as sensor 12 (FIG. 1) to measure biological characteristics of a patient such as patient 40 (FIG. 2). Respiration signal 505 may also be derived from other biosignals including transthoracic impedance signals, capnograph signals, nasal thermistor signals, and/or electrocardiogram (EKG) signals. The respiration signal and/or one or more signals that may be used to derive the respiration signal may be real-time signals or may be signals previously received and stored in memory, for example, ROM 52 (FIG. 2) or RAM 54 (FIG. 2).

In an embodiment, the respiration signal obtained at step 720 may be derived from a PPG signal. The PPG signal may be obtained by processing another, preliminary PPG signal. For example, a preliminary PPG signals may be obtained using, e.g., sensor 12 (FIG. 1) and processed using a processor such as processor 412 (FIG. 4) or microprocessor 48 (FIG. 2) in a system similar or identical to pulse oximetry system 10 (FIG. 1). For example, the preliminary signal may be processed using low-pass filters, noise-component removal techniques, and/or interpolation methods, that may remove various undesirable artifacts that may be present in the preliminary signal. As another example, one or more preliminary PPG signals may be selected and mirrored to create the PPG signal used to derive a respiration signal using techniques similar or identical to those described in Watson, U.S. Provisional Application No. 61/077,092, filed Jun. 30, 2008, entitled "Systems and Method for Detecting Pulses," and McGonigle et al., U.S. application Ser. No. 12/437,317, filed May 7, 2009, entitled "Concatenated Scalograms," which are incorporated by reference herein in their entirety. As yet another example, a preliminary PPG signal may be analyzed to calculate regions having at least a threshold level of stability and/or consistency using techniques similar or identical to those described in Watson et al., U.S. application Ser. No. 12/437,326, filed May 7, 2009, entitled "Consistent Signal Selection By Signal Segment Selection Techniques," which is incorporated by reference herein in its entirety.

The respiration signal obtained in step 720 may be derived from a PPG signal by generating a scalogram from a received PPG signal. For example, a scalogram may be derived using the same method (e.g., using continuous wavelet transforms) that was used to derive the scalograms shown in FIGS. 3(a), 3(b), and 3(c). The scalogram of the wavelet transform may be generated or otherwise obtained using, for example a processor such as processor 412 (FIG. 4) or microprocessor 48

(FIG. 2). In addition to the scalogram, other parts of the wavelet transform may be determined. For example, the transform modulus, phase, real, and/or imaginary pails may be generated in addition to the scalogram.

The resultant scalogram may include bands and ridges corresponding to at least one area of increased energy. A respiration band of the scalogram may generally reflect the breathing pattern of a patient, e.g., patient 40 (FIG. 2). These bands may be extracted from the scalogram using, for example, a processor such as processor 412 (FIG. 4) or microprocessor 48 (FIG. 2), using any suitable method. The respiration band of the scalogram may be identified using characteristics of the scalogram including the energy and structure of the scalogram, and the signal-to-noise levels in various regions of scalogram. In one embodiment, this information may be calculated one or more times using different time-window sizes. The number and type of time-window sizes that are used may depend on the anticipated respiration rate, the available computational resources (e.g., the amount of ROM 52 (FIG. 2) and/or RAM 54 (FIG. 2) and the speed of processor 412 (FIG. 4) and/or microprocessor 48 (FIG. 2)), as well as on possible input derived from user inputs 56 (FIG. 2).

The respiration signal may be derived from the amplitude and/or scale modulation observed in the respiration band (e.g., respiration band B in FIG. 3(*c*)). The respiration signal may also may be derived after further analysis of the scalogram including, for example, secondary wavelet feature decoupling. This secondary wavelet feature decoupling of a ridge allows for information concerning the band of interest (e.g., respiration band B in FIG. 3(*c*)) to be made available as secondary bands (e.g., band C and band D in FIG. 3(*d*)). The ridges of the secondary bands may serve as instantaneous time-scale characteristic measures of the underlying signal components causing the secondary bands, which may be useful in analyzing the signal component associated with the underlying physical process causing the primary band of interest (e.g., the respiration band B) when band B itself may be obscured. By extracting and further analyzing a respiration band in the scalogram, a respiration signal may be extracted from the scalogram when the respiration band itself is, for example, obscured in the presence of noise or other erroneous signal features.

At step 730 signal peaks may be identified from the respiration signal obtained in step 720. Signal peaks may be found, e.g., using any suitable signal processing technique, including a zero-crossing technique, a root-finding technique, an analytic curve-fitting technique, and/or a numerical analysis of the derivatives of the selected portion of the signal. These and other techniques may be implemented in pulse oximetry system 10 (FIG. 1) by processor 412 (FIG. 4), microprocessor 48 (FIG. 2), ROM 52 (FIG. 2), and/or RAM 54 (FIG. 2). Additionally, the parameters that may be used by suitable signal processing techniques, e.g., tolerance values and sensitivity levels, may be controlled by a user or patient using, e.g., using user inputs 56 (FIG. 2). Signal peaks that are identified may be displayed, for example, on monitor 26 (FIG. 1) or display 20 or 28 (both of FIG. 1). Alternatively, a portion of the respiration signal generated at step 730 may be displayed on a monitor, and a user may choose or otherwise influence which peaks are selected using, for example, user inputs 56 (FIG. 2).

At step 740 one or more signal peak thresholds may be selected or determined. Signal peak thresholds may calculated using any suitable signal processing and analysis techniques. For example, signal peak thresholds may be related to a mean, median, mode, range, standard deviation, or percentile of the signal peaks identified at step 730. Signal peak threshold values may be determined based on an initial set of signal peak values. Signal peak thresholds may then be replaced or updated periodically or continuously based on newer incoming signal peak values. Alternatively, signal peak thresholds may be set to predetermined values based on historical or idealized respiration signal data or based on any other suitable data. These and other techniques may be implemented in pulse oximetry system 10 (FIG. 1) by processor 412 (FIG. 4), microprocessor 48 (FIG. 2), ROM 52 (FIG. 2), and/or RAM 54 (FIG. 2). Additionally, the parameters that may be used by suitable signal processing techniques, e.g., tolerance values and sensitivity levels, may be controlled by a user or patient using, e.g., using user inputs 56 (FIG. 2). Signal peak thresholds may be displayed, for example, on monitor 26 (FIG. 1) or display 20 or 28 (both of FIG. 1). Alternatively, the portion of the respiration signal obtained in step 720 may be displayed on a monitor, and a user may choose or otherwise influence signal peak thresholds using, for example, user inputs 56 (FIG. 2).

Illustrative plot 500 (FIG. 5) includes a single, upper threshold 510. Signal peaks that exceed the upper threshold value may be reduced. Illustrative plot 600 (FIG. 6) includes an additional, lower threshold 620. Signal peaks that exceed the lower threshold value may be increased, but signal peaks that have amplitudes below the lower threshold may be left unchanged. A minimum threshold (not illustrated) may reduce or eliminate signal peaks that have amplitudes below the minimum threshold values or may prevent signal peaks below this minimum threshold from being modified. Other threshold types may also be provided. The number and type of signal peak thresholds used to normalize respiration features within a respiration signal may be determined by processor 412 (FIG. 4), microprocessor 48 (FIG. 2) based on any suitable signal processing and analysis techniques. For example, the particular type of signal peak thresholds to be used may be determined based on the respiration signal to be processed. Additionally, the number and type of signal peak thresholds used to process a respiration signal may be controlled by a user or patient using, e.g., using user inputs 56 (FIG. 2). One or more signal peak thresholds may be displayed, for example, on monitor 26 (FIG. 1) or display 20 or 28 (both of FIG. 1) and the user may choose or otherwise the number and type of signal peak thresholds using, for example, user inputs 56 (FIG. 2).

At step 750, one or more the signal peaks identified in step 730 may be adjusted based on the signal peak thresholds determined in step 740. The signal adjustment may be performed by a processor such as processor 412 (FIG. 4) or microprocessor 48 (FIG. 2). For example, signal peaks that exceed an upper threshold value may be reduced in value and/or signal peaks that exceed a lower threshold may be increased in value. These adjustments may be used to provide a normalized respiration signal. Alternatively or additionally, the adjustments may be made within the one or more scalograms used to generate the original respiration signal. The adjusted scalograms may be processed further to determine or estimate additional information. For example, two or more scalograms having adjusted respiratory features may be concatenated together and processed to improve the computation of information such as respiration information using techniques similar or identical to those described in McGonigle et al., U.S. application Ser. No. 12/1437,317, filed May 7, 2009, entitled "Concatenated Scalograms," which was previously incorporated by reference herein.

One approach for modifying the value of an identified respiration signal peak is to linearly rescale a signal segment associated with the signal peak. Referring to respiratory signal 505 (FIG. 5), signal peak 511 exceeds upper threshold 510. Therefore, a signal segment defined by the zero crossing (or any other suitable points) before and after signal peak 511, i.e., points 511b and 511c, may be resealed by a constant factor (less than unity). In an embodiment, the constant factor may be set to a value such that the adjusted signal peak (e.g., 511a) for a given signal peak (e.g., 511a) is less than or equal to the signal peak threshold value or any other suitable value (e.g., a mean value). This value may be set such that all adjusted peak values will be similar. Alternatively, the same constant factor may be used irrespective of the actual signal peak value. In an embodiment, only the portion of the signal that crosses a threshold may be resealed. For example, referring to respiratory signal 505 (FIG. 5) and according to this embodiment, only the respiration signal segment between signal points 511d and 511e may be adjusted. In an embodiment, a nonlinear resealing value may be used whereby the change in value of a respiration signal segment associated with a signal peak may be related in some way to the distance between the signal peak value and an average value of the signal. Nonlinear resealing values may also be related to a distance between a signal peak and, for example, the threshold value, a desired value, or another predetermined value. The nonlinear relationship may be smoothly nonlinear or may be made up of discreet linear scaling factor values.

At step 760 a respiration parameter may be generated based on the normalized respiration signal adjusted in step 750. For example, a respiration rate may be determined or estimated from the adjusted respiration signal using any suitable approach. The respiration rate may be represented by a number from 1 to 100, where a larger number indicates a larger respiration rate (any other suitable number range could be used instead). The determination of the respiration rate may be performed, for example, by processor 412 (FIG. 4) or microprocessor 48 (FIG. 2), and may additionally depend on parameters entered by a user through user inputs 56 (FIG. 2). To estimate a respiration rate the processor may use, for example, maximum-likelihood techniques to combine data when the prior probability of a given respiration rate is known, and Neyman-Pearson combining techniques may be used when the prior probability of a given respiration rate is unknown.

At step 770 the respiration parameter determined or estimated from the respiration signal in step 760 may be reported. For example, a respiration rate may be reported by generating an audible alert or, for example, using speaker 22 (FIG. 2) as well as possibly through other audio devices, generating an on-screen message, for example, on display 20 (FIG. 1) or display 28 (FIG. 1), generating a pager message, a text message, or a telephone call, for example, using a wireless connection embedded or attached to a system such as system 10 (FIG. 1), activating a secondary or backup sensor or sensor array, for example, connected through a wire or wirelessly to monitor 14 (FIG. 1), or regulating the automatic administration medicine, for example, which is controlled in part or fully through a system such as system 10 (FIG. 1). Additionally, the respiration rate may be reported on a display such as display 20 (FIG. 1) or display 28 (FIG. 1) in graphical form using, for example, a bar graph or histogram. The respiration parameter may also be reported to one or more other processes, for example, to be used as part of or to improve the reliability of other measurements or calculations within a system such as pulse oximetry system 10 (FIG. 1).

Figure 8:
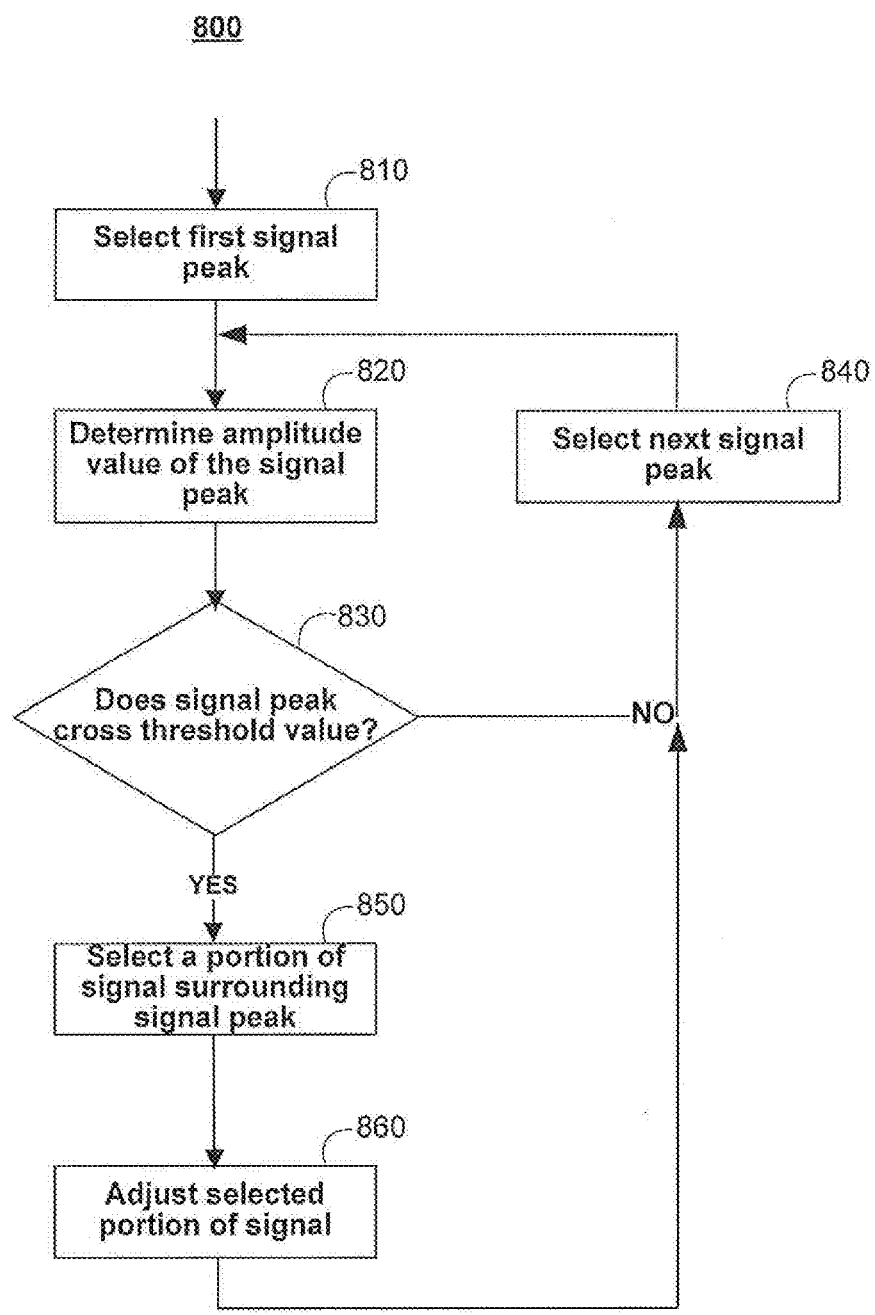
FIG. 8 depicts an illustrative process for adjusting one or more respiration signal peaks in accordance with an embodiment.

FIG. 8 depicts an illustrative process for adjusting one or more signal peaks in a signal, e.g., respiration signal 505 (FIG. 5), in accordance with some embodiments. Process 800 may be implemented in a pulse oximetry system such as pulse oximetry system 10 (FIG. 1), and the steps of process 800 may be carried out using a processor such as processor 412 (FIG. 4) or microprocessor 48 (FIG. 2). Process 800 may correspond to a further embodiment of process 700, and more particularly, may correspond to a further embodiment of step 750 of FIG. 7. Process 800 may start at step 810. At step 810, a first signal peak is selected. For example, at step 810, process 800 may select one of the signal peaks of a respiration signal identified by process 700 (FIG. 7) at step 730. The first signal peak may correspond to the first-occurring signal peak in time, e.g. signal peak 511 (FIG. 5) of respiration signal 505, and/or it may correspond to the first signal peak found through a suitable signal processing algorithm, such as an extrema-finding algorithm. Once the location of a first peak has been found, at step 810 an amplitude value of the first signal peak may be determined at step 820.

At step 830, it is determined whether the signal peak crosses a threshold value. The value of the signal peak may be compared to one or more signal peak threshold values determined by process 700 (FIG. 7) at step 750. For example, for respiration signal 505 (FIG. 5) it may be determined that signal peak 511 exceeds threshold 510. As another example, for respiration signal 605 (FIG. 6) it may be determined that signal peak 621 exceeds threshold 620. Signal peak 611 exceeds both thresholds 610 and 620. In this instance, only the higher threshold (i.e., threshold 610) is considered. If the signal peak does not cross any threshold values, the next signal peak is selected at step 840 and process 800 continues until there are no more signal peaks.

If it is determined that the signal peak crosses a threshold value, at step 850 a portion of the signal surrounding the signal peak may be selected. For example, signal peak 511 (FIG. 5) of respiration signal 505 exceeds the value of signal peak threshold 510. As described above, the signal segment defined by the zero crossing before and after signal peak 511, i.e., points 511b and 511c, may be selected. Alternatively, the signal segment defined by the threshold crossing before and after signal peak 511, i.e., points 511d and 511e, may be selected. Any other suitable portion of the signal between the selected signal peak and adjacent signal peaks may also be selected. At step 860 the selected portion of the signal may be adjusted using linear or nonlinear scaling techniques, as described above. Finally, the next signal peak is selected at step 840 and process 800 continues until there are no more signal peaks.

Figure 9:
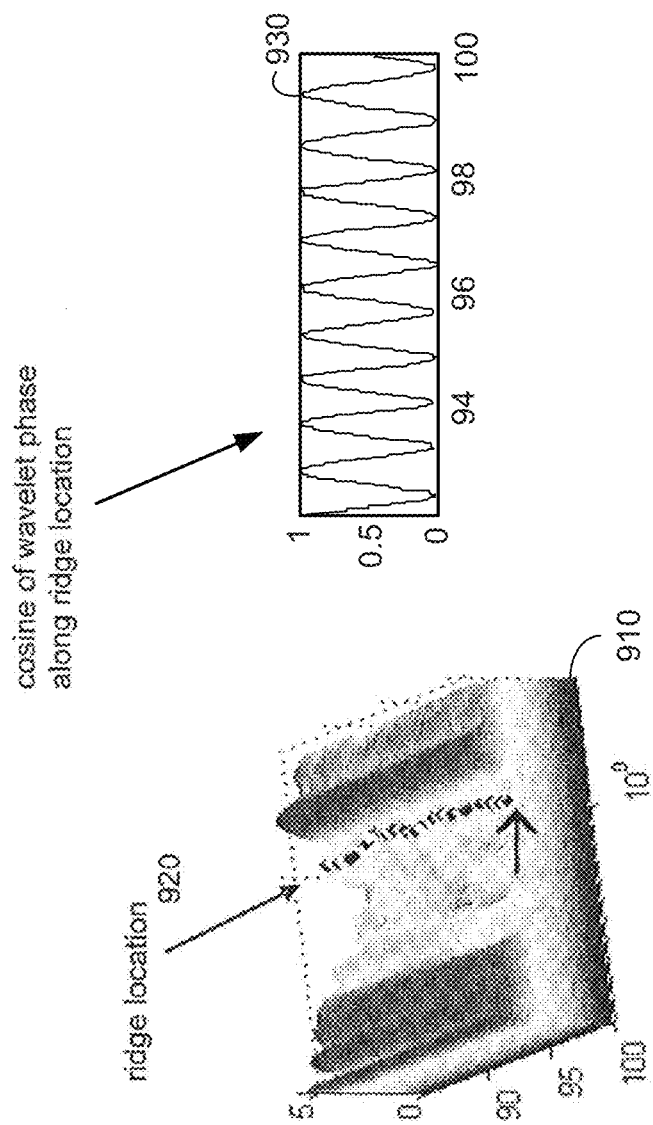
FIG. 9 depicts an additional illustrative process for generating a normalized respiration signal from a scalogram in accordance with an embodiment.

FIG. 9 depicts an additional illustrative process for generating a normalized respiration signal from a scalogram 910. Scalogram 910 of the wavelet transform may be generated or otherwise obtained at least in part from a received PPO signal using, for example a processor such as processor 412 (FIG. 4) or microprocessor 48 (FIG. 2). Scalogram 910 includes wavelet phase information from a received PPG signal in the region of the feature scales in wavelet space. Similar to the respiration ridge within respiration band B in the scalogram illustrated FIG. 3(c) and the respiration ridge within a secondary bands C and D in FIG. 3(d), which represent amplitude and/or scale modulation relating to respiration features as a function of time, ridge location 920 includes local phase values relating to respiration features as a function of time. A sinusoidal function indicative of respiration phase and having normalized height values may be generated from these local phase values by taking the sine or cosine of these values. Plot 930 is an illustrative cosine signal of wavelet phase values along ridge location 920. Alternatively, an inverse wavelet transform may be performed on the local transform phase values along ridge location 920 to generate a normalized respiration signal.

It will also be understood that the above method may be implemented using any human-readable or machine-readable instructions on any suitable system or apparatus, such as those described herein.

The foregoing is merely illustrative of the principles of this disclosure and various modifications may be made by those skilled in the art without departing from the scope and spirit of the disclosure. The following claims may also describe various aspects of this disclosure.

What is claimed is:

1. A method for processing a respiration signal comprising: using a processor for:
   obtaining the respiration signal, wherein the respiration signal comprises a plurality of signal peaks;
   identifying one or more signal peaks of the plurality of signal peaks;
   determining a signal peak threshold for the respiration signal based at least in part on the identified one or more signal peaks;
   adjusting one or more signal peaks of the plurality of signal peaks based at least in part on the signal peak threshold to generate an adjusted respiration signal, wherein at least one of the plurality of signal peaks remains unchanged in the adjusted respiration signal;
   determining a respiration parameter based at least in part on the adjusted respiration signal; and
   reporting the determined respiration parameter.

2. The method of claim 1, wherein the respiration signal is obtained based at least in part on data received from a sensor.

3. The method of claim 1, further comprising generating the respiration signal from a PPG photoplethysmograph (PPG) signal, a transthoracic impedance signal, a capnograph signal, a nasal thermistor signal, or an electrocardiogram (EKG) signal.

4. The method of claim 3, wherein generating the respiration signal from the PPG signal comprises:
   obtaining a PPG signal;
   generating a scalogram based at least in part on received PPG signal;
   analyzing one or more features within the scalogram; and
   generating the respiration signal based at least in part on the one or more analyzed features.

5. The method of claim 1, wherein determining a signal peak threshold comprises determining an upper signal peak threshold value.

6. The method of claim 5, wherein adjusting one or more signal peaks of the plurality of signal peaks comprises:
   comparing an amplitude value of a signal peak of the plurality of signal peaks with the upper signal peak threshold value; and
   reducing the amplitude value of the signal peak to a value less than the upper signal peak threshold value.

7. The method of claim 5, wherein determining a signal peak threshold further comprises determining a lower signal peak threshold value.

8. The method of claim 7, wherein adjusting one or more signal peaks of the plurality of signal peaks comprises:
   comparing an amplitude value of a signal peak of the plurality of signal peaks with the lower signal peak threshold value; and
   increasing the amplitude value of the signal peak to a value greater than the lower signal peak threshold value.

9. The method of claim 1, wherein adjusting one or more signal peaks of the plurality of signal peaks comprises:
   selecting a portion of the respiration signal surrounding a signal peak of the plurality of signal peaks; and
   adjusting the selected portion of the respiration signal.

10. The method of claim 9, wherein adjusting the selected portion of the respiration signal comprises resealing the selected portion by a constant factor.

11. The method of claim 1, wherein the respiration parameter comprises a respiration rate and/or respirations effort.

12. A system for processing a respiration signal system comprising:
   a processor coupled to a sensor, wherein the processor is configured to:
      obtain the respiration signal, wherein the respiration signal comprises a plurality of signal peaks;
      identify one or more signal peaks of the plurality of signal peaks;
      determine a signal peak threshold for the respiration signal based at least in part on the identified one or more signal peaks;
      adjust one or more signal peaks of the plurality of signal peaks based at least in part on the signal peak threshold to generate an adjusted respiration signal, wherein at least one of the plurality of signal peaks remains unchanged in the adjusted respiration signal;
      determine a respiration parameter based at least in part on the adjusted respiration signal; and
      report the determined respiration parameter.

13. The system of claim 12, wherein the sensor is configured to receive data and wherein the respiration signal is obtained based at least in part on data received from the sensor.

14. The system of claim 12, wherein the respiration signal is obtained from a PPG photoplethysmograph (PPG) signal, a transthoracic impedance signal, a capnograph signal, a nasal thermistor signal, or an electrocardiogram (EKG) signal.

15. The system of claim 12, wherein the processor is further configured to:
   obtain a PPG signal;
   generate a scalogram based at least in part on received PPG signal data;
   analyze one or more features within the scalogram; and
   generate the respiration signal based at least in part on the one or more analyzed features.

16. The system of claim 12, wherein the system determined signal peak threshold comprises an upper signal peak threshold value.

17. The system of claim 16, wherein the processor is further configured to:
   compare an amplitude value of a signal peak of the plurality of signal peaks with the upper signal peak threshold value; and
   reduce the amplitude value of the signal peak to a value less than the upper signal peak threshold value.

18. The system of claim 16, wherein the determined signal peak threshold comprises a lower signal peak threshold value.

19. The system of claim 18, wherein the processor is further configured to:
   compare an amplitude value of a signal peak of the plurality of signal peaks with the lower signal peak threshold value; and
   increase the amplitude value of the signal peak to a value greater than the lower signal peak threshold value.

20. The system of claim 12, wherein the processor is further configured to:
   select a portion of the respiration signal surrounding a signal peak of the plurality of signal peaks; and
   adjust the selected portion of the respiration signal.

21. The system of claim 20, wherein the processor is further configured to rescale the selected portion by a constant factor.

22. The system of claim 12, wherein the determined respiration parameter comprises a respiration rate and/or respiration effort.

* * * * *